United States Patent [19]
Wymond

[11] Patent Number: 6,015,418
[45] Date of Patent: Jan. 18, 2000

[54] FINGERNAIL AND TOENAIL DRILL

[76] Inventor: Tyler R. Wymond, 2694 Stony Fork Way, Boise, Id. 83706

[21] Appl. No.: 08/974,523

[22] Filed: Nov. 19, 1997

[51] Int. Cl.⁷ ................................................ A61B 17/32
[52] U.S. Cl. .......................................... 606/167; 606/188
[58] Field of Search .................................. 606/167, 166, 606/186, 170, 168, 79, 96, 86; 206/379; 408/127

[56] References Cited

U.S. PATENT DOCUMENTS

| | | | |
|---|---|---|---|
| 460,138 | 9/1891 | Hornberger | 606/188 |
| 1,390,720 | 9/1921 | Powers | 606/167 |
| 2,713,863 | 7/1955 | Handerson | 606/188 |
| 4,414,974 | 11/1983 | Dotson et al. | 606/167 |
| 4,844,070 | 7/1989 | Dee | 606/167 |
| 5,387,222 | 2/1995 | Strickland | 606/167 |
| 5,569,288 | 10/1996 | Yoon | 606/185 |
| 5,586,991 | 12/1996 | Yoon | 606/185 |

*Primary Examiner*—Michael Buiz
*Assistant Examiner*—Tan-Uyen T. Ho
*Attorney, Agent, or Firm*—Ken J. Pedersen; Barbara S. Pedersen

[57] ABSTRACT

Embodiments of a fingernail or toenail drilling instrument are described for relieving the pressure of an injured appendage beneath the finger- or toenail. The drilling instrument has a shaft with a sharp, pointed tip and preferably has a generally concave surface, that may be part of an interior hollow surface near the tip point or that may be a concave outer surface near the tip point, making the shaft an effective piercing and drilling instrument. The invented drill may include a holder covered by a removable case, and the case may be adapted to snap onto the holder as an extension for use as a handle. Preferably, the case exterior surface has texture or protrusions for creating a gripping surface for improving accuracy and preventing the drill from slipping the user's fingers. This drilling instrument can be available without a prescription because it conceivably is not usable or adaptable to be a fluid-injection shaft. The drilling instrument is hand-powered by the user's fingers rotating it around its longitudinal axis and gently pressing it into the nail; therefore, no motor or other power source is needed. The invented drilling instrument allows an injured party or the person giving first aid to save the expense of a doctor visit and to save time and expense over obtaining a prescription. Also, with this invention, the doctor will be spared the time involved with dealing with a minor problem that could be easily handled by the injured individual without his assistance.

11 Claims, 4 Drawing Sheets

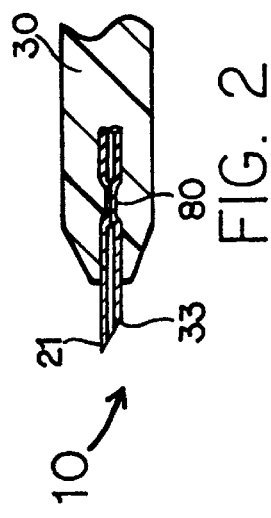
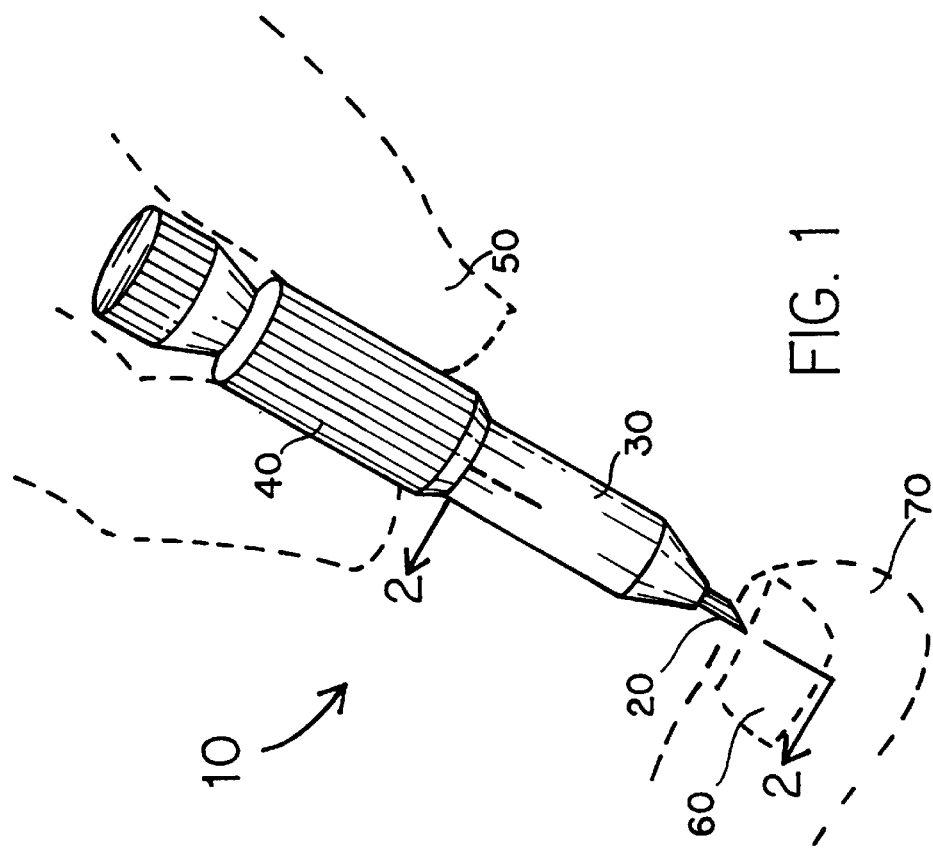

FINGERNAIL AND TOENAIL DRILL

BACKGROUND OF THE INVENTION

1. Field of the Invention

This invention relates to a method of relieving swelling of a human appendage, such as a finger or toe, when the swelling occurs underneath the finger- or toenail. More specifically, this invention is a non-motorized drill that is fashioned to safely perforate a nail and/or skin to relieve the swelling pressure of the wound.

2. Related Art

A common type of human injury occurs when an appendage is smashed. Some circumstances under which such an event happens are when wielding a hammer and missing the mark, inadvertently having fingers slammed by a closing door, or dropping a heavy object on one's toe, etc. In all such cases, but not relegated to those just mentioned, the ultimate result is a very painful bruise and attendant swelling of the affected appendage. If the area were not covered by a fingernail or toenail, gaining relief would be relatively simple, but, in order to relieve the swelling under a nail, the nail needs to be perforated in order to also perforate the skin of the swollen area beneath the nail. Once the nail and skin are perforated, fluids may ooze out to relieve pressure.

In the past, people have burned the nail with a red-hot wire, or doctors in emergency rooms have used the tip of a hypodermic needle to poke through the nail and thus perforate the nail and/or skin tissue in the injured area. Still, there is needed an over-the-counter drill for swelling under a human nail. A drill is needed that is economical and easy and safe to use.

SUMMARY OF THE INVENTION

The invention comprises a drilling instrument that has beneficial drilling features to safely and accurately drill through a human nail, while being simple and economical to manufacture and use. Another object of the invention is to provide an instrument that optimizes accuracy and safety during drilling. The invented drilling instrument may be offered over-the-counter, that is, without a prescription, and is not reasonably modifiable to be used for a dangerous or illegal purpose. Another object of the invention is to provide an aseptic, small, easily-storable unit for inclusion in first-aid kits and other emergency supplies. With the invented instrument, an injured party or the person giving first aid may save the expense of a doctor visit or treat the injury in advance of a visit to the doctor, for example, during the night and weekend hours when economical medical care is not available.

The invented drilling instrument is designed to be hand-held and rotated or twisted in order to pierce a fingernail and subsequently penetrate the skin under the nail, if necessary, to relieve the pressure and pain when said area has been injured. The drill has the attributes of being fine-pointed, sharp, and hollow near the tip, in order to provide excellent piercing and drilling qualities and to minimize pain and additional injury to the patient's finger or toe. The shaft of the invented drilling instrument may be hollow substantially along its axial length, so that the hollow interior surface near the shaft tip features sharp interior cutting edges as well as sharp exterior cutting edges, and creates an interior space for receiving nail and tissue from the drilling procedure. Alternatively, the shaft may be hollow only near the shaft tip or, instead of being hollow, may have a concave exterior surface on at least one side of the tip. The drill shaft is preferably ensconced in a plastic casing that acts as both handle and a cover that helps keep the shaft aseptic once it has been sterilized. In use, the aseptic cover is removed from covering the single sharp drill tip and then snapped onto the other end of the shaft holder to act as a handle.

BRIEF DESCRIPTION OF THE DRAWINGS

FIG. 1 presents a perspective view of one embodiment of the invented fingernail drill.

FIG. 2 provides a cross-sectional view of the substantially hollow shaft of the fingernail drill of FIG. 1 as it is encased in the holder of the drill.

DETAILED DESCRIPTION OF THE PREFERRED EMBODIMENT

Figure 3:
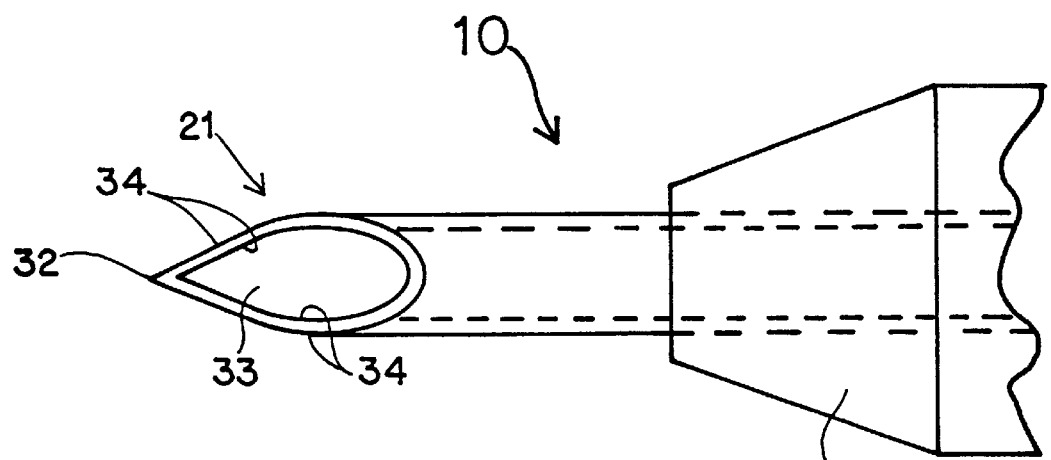
FIG. 3 is an enlarged side view of the shaft of the embodiment of FIG. 1.

Referring to the Figures, there are shown several embodiments of the invented fingernail and toenail drilling instrument, also referred to herein as a "drill". The preferred use of the invented drill is to alleviate pressure underneath the nail of an injured appendage by delicately and precisely drilling through the nail and any skin acting to encase the swelling area.

The preferred embodiment of a fingernail drill 10 in its entirety, and as viewed when ready to use, is shown in FIG. 1. The drill 10 comprises a shaft 20, which is fine, sharp, and hollow at its single distal end, or "tip" 21. This shaft 20 is held firmly in position by the holder 30 portion of the drill 10, which, in this figure is only partially seen, because the case 40 is covering the upper portion 31 of holder 30. The case 40 is snapped onto the upper portion 31 of holder 30 so that it creates a handle, as shown in FIG. 1, by a person's fingers 50 holding the drill 10 by gripping case 40. By thus gripping the case 40, the user may position and manipulate the drill 10 exactly where it needs to be in order for the shaft tip 21 to pierce and then drill through the nail 60 on injured appendage 70.

FIG. 2 illustrates one embodiment of a hollow shaft 20, which is hollow substantially alone its entire longitudinal axis. The embodiment of FIG. 2 is made hollow at and near the tip 21, by using a hollow, metal tube cut diagonally and shaped to create a pointed and sharp-edged tip and crimped as shown at pinch 80 on the drawing, before being installed in a holder 30. The tip 21 provides a very fine point 32 and very sharp inner and outer edges 34, as shown in the detail of FIG. 3. The hollow space 33 near the point 32 serves to receive the drilled nail material and any other tissue or fluid that is removed from its normal location by the drill. Thus, the hollow space 33 allows relief of pressure and pain even as the drilling is being done, by collecting the material from the kerf or hole created by the drilling is hollow at and near the tip 21.

This pinch 80 is located in the body of the shaft 20 which is encased and held firm by solid plastic holder 30. The crimped shaft 20 serves to provide additional securement of the shaft 20 in the molded plastic holder 30, preventing any radial or axial movement of the shaft 20 relative to the holder 30. Additionally, the crimped shaft 20 renders the shaft interior space "obstructed", to serve as additional insurance that the shaft cannot be modified for any improper use, for example, for adaptation as part of a syringe. Alternatively, an un-crimped shaft may also be used, and, because one of its open ends is securely embedded in the plastic holder and the shaft is preferably only about 2–5 cm in length, it is clearly not adaptable as part of a syringe.

Figure 4:
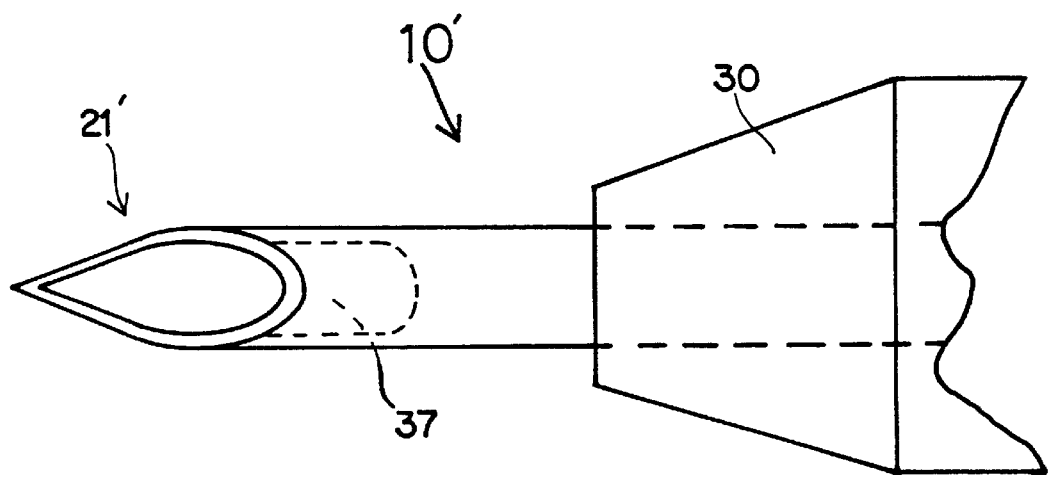
FIG. 4 is an enlarged side view of an alternative shaft of the invented drill.
Figure 5:
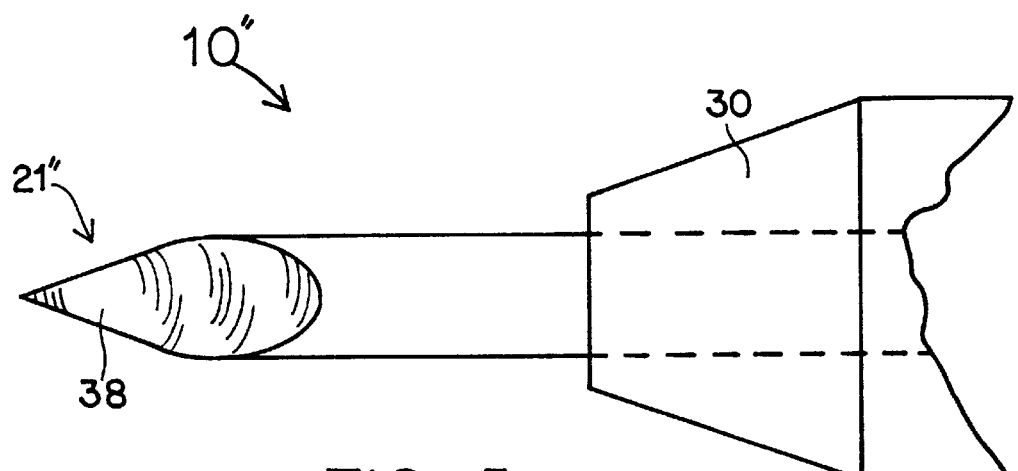
FIG. 5 is an enlarged side view of an alternative shaft of the invented drill, having a concave tip surface.

Alternatively, the shaft may be a substantially-solid shank with a hollow or otherwise concave surface near the point of the tip 21', as shown in FIGS. 4 and 5. The concave surface may result from the tip 21' being hollow a short distance into the shaft, as shown by the shorter interior space 37 of drill 10' in FIG. 4. Or, there may be an inwardly-curved side surface 38 on one side of the tip 21", as in drill 10" in FIG. 5. The surface 38 curves in from side edge to side edge of the tip. The inwardly-curved side surface 38, similarly as the hollow space 37 of the hollow tip 21', provides an area for relief and collection of tissue and fluid during drilling.

Figure 6:
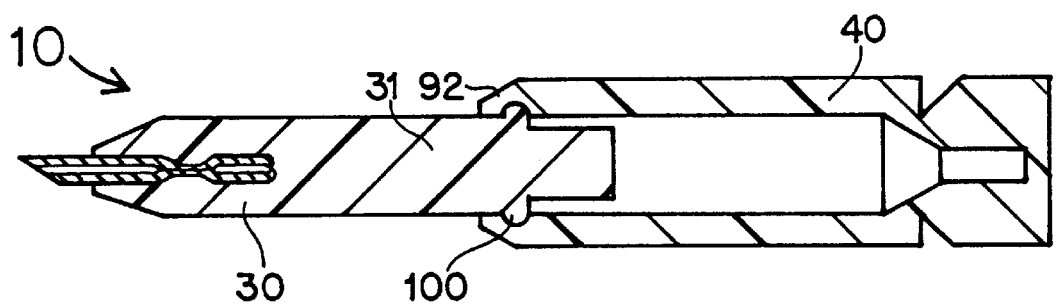
FIG. 6 is a cross-sectional view of the embodiment of FIG. 1, demonstrating how the case snaps onto the shaft holder to be create a comfortable handle.

FIG. 6 addresses the use of the case 40 as a handle, giving the user a longer piece than simply the holder 30 to grip and manipulate when pressing and rotating the shaft 20 to pierce and drill a nail. The holder 30, in which the shaft 20 is firmly and preferably permanently embedded, is designed with ring 100 or other slight protrusion near the end (the proximal end) of the holder 30 opposite from the end (the distal end) from which the shaft 20 emerges. The ring 100 protrudes generally radially out from the holder 30. The case distal end 92 snaps over and frictionally engages this ring 100, so the holder 30 extends from the case 40 for use and is secured firmly in position relative to the case 40. The holder 30 is preferably engaged sufficiently to prevent movement of the holder 30 relative to the case 40 in both axial and rotational directions, until the user purposely twists the case 40 relative to the holder 30 or removes the case 40 from the holder 30.

Figure 7:
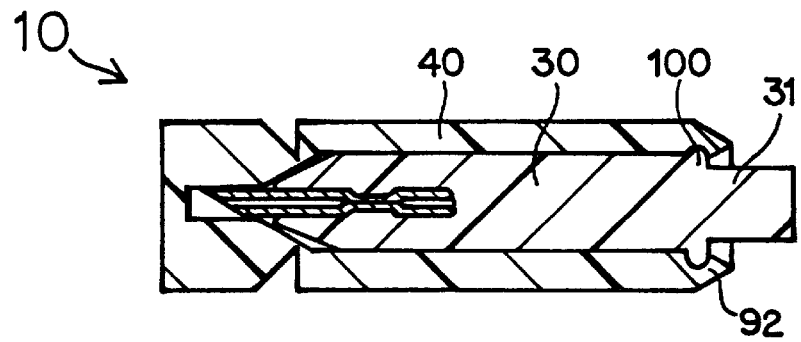
FIG. 7 demonstrates how, for safety and aseptic storage, the case can snap over the point when the drill is not in use.
Figure 8:
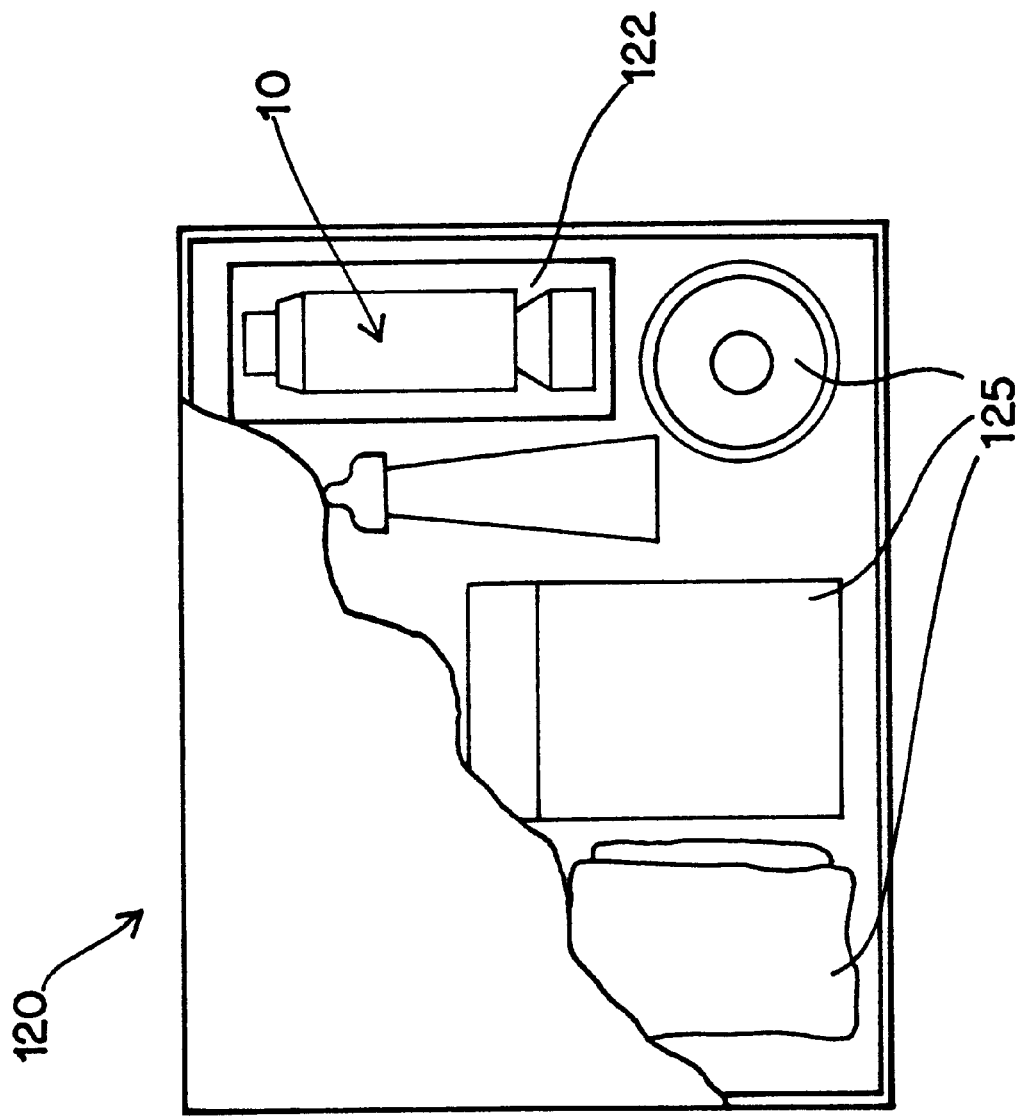
FIG. 8 is a schematic top view of another embodiment of the invented drill, packaged as part of a first aid kit.

When the drill 10 is not is use, as demonstrated in FIG. 7, the case 40 can be pulled of the ring 100, turned around, placed over the shaft 20 on holder 30, and again be snapped into place over the ring end of the holder 30. Thus, the case 40 may be used to cover the sharp tip, to provide a measure of safety before and after use. Further, at the time of purchase, this case 40 provides an aseptic cover for the shaft 20 until such time as the drill 10 is used.

Preferably, the metal shaft and the holder and case are materials that can withstand sterilization, including the extreme conditions and times currently used for sterilization. Thus, once properly sterilized and aseptically packaged, there should be little or no concern for infection of the injured patient, provided careful, clean procedures are followed during and after drilling.

Preferably, the invented drilling instrument is manufactured from high quality but disposable components. The preferably stainless steel shaft is combined with sturdy plastic, with the case 40 being resilient enough to snap over the holder 30. Disposal of the drill 10 is easily done, in accordance with safe procedures for disposing of any material that has been in contact with human body fluids.

Preferably, the drill 10 is supplied in first aid kit form, so that a nurse, office staff member, or a parent, for example, may quickly and safely tend to a smashed finger or toe, instead of waiting until tremendous pressure and pain develop. A kit 120 preferably contains one or more drill units, wherein a drill 10 is sterilely wrapped in a durable, but easily-opened, at least partially transparent medical packaging 122. The kit 120 may also contain other medical supplies 125, such as bandages, antiseptics, smelling salts, etc., as may be part of a standard emergency kit.

The user may twist or rotate the drill 10 of this invention in his fingers to cause the shaft to spin, that is, to rotate on its longitudinal axis, to bore a tiny and accurate hole in the patient's nail. Because of the sharpness and the concavity (including hollowness) of the shaft tip, the drill tip effectively drills through the nail without adding significantly to the pain of the patient.

The drill of the invention may be described, therefore, as having a drill tip that is pointed and hollow or that has a concave tip surface. The hollow or concave tip results in the tip having a curved surface, either the generally cylindrical inner surface of a hollow tip or the inwardly-curved outer surface of a concave tip. The drill shaft preferably has a main body that is at least partially solid, either by the body being crimped to close-off a longitudinal passage or by the body being manufactured to be substantially solid. Thus, the shaft may be described as preferably being solid in radial cross-section (that is, transverse to the axis) in at least one location along the longitudinal axis. Preferably, the shaft is a single, unitary piece of metal, and is not removable from the holder. The shaft of the invented drill preferably is not curved in that it has a generally straight longitudinal axis.

The invented drilling instrument preferably is made only of the shaft, the holder and the case, resulting in an economical, disposable unit. Preferably, the drill is hand-held and between about 3–6 inches in total length when in use. The drill preferably has no other source of power or movement besides the hand of the user, and, therefore, does not include any motor, battery, or instrumentation.

Although this invention has been described above with reference to particular means, materials and embodiments, it is to be understood that the invention is not limited to these disclosed particulars, but extends instead to all equivalents within the scope of the following claims.

I claim:

1. A drilling instrument for use on a nail of a human appendage, the drilling instrument comprising:

a shaft having a tip and a body and a longitudinal axis, the body having a proximal end opposite the tip and the body being solid in radial cross-section in at least one location along its longitudinal axis, the tip having a single sharp point and being hollow at the sharp point;

a handle connected to said shaft for grasping by a user for causing the shaft to drill through the nail.

2. A drilling instrument as in claim 1, wherein the shaft is a hollow tube and has a crimp along the longitudinal axis to create a solid portion of the body.

3. A drilling instrument as in claim 1, wherein the shaft body is solid from about 3 mm from the point to the proximal end.

4. A drilling instrument as in claim 1, wherein the shaft body is solid from about 15 mm from the point to the proximal end.

5. A drilling instrument as in claim 1, further comprising a shaft holder secured to the body of the shaft, and a case that is a separate unit from the shaft holder but that is removably snapped onto the shaft holder for use as a handle and for use as a shaft cover.

6. A drilling instrument for use on a nail of a human appendage, the drilling instrument comprising:

a shaft having a tip and a body and a longitudinal axis, the body having a proximal end opposite the tip and the body being solid in radial cross-section in at least one location along its longitudinal axis, the tip having a single sharp point and having a concave outer surface at the sharp point;

a handle connected to said shaft for grasping by a user for causing the shaft to drill through the nail.

7. A drilling instrument as in claim 6, wherein the shaft body is solid from about 3 mm from the point to the proximal end.

8. A drilling instrument as in claim 6, wherein the shaft body is solid from about 15 mm from the point to the proximal end.

9. A drilling instrument for use on a nail of a human appendage, the drilling instrument consisting of:

a shaft having a tip and a body and a longitudinal axis, the body having a proximal end opposite the tip and the body being solid in radial cross-section in at least one location along its longitudinal axis, the tip having a single sharp point and being hollow at the sharp point;

a holder secured to said shaft; and a case removably connected to the holder;

wherein the case and holder are adapted to be removably connected together in two positions, one position being with the case extending from the holder opposite the shaft and another position being with the case extending from the holder to enclose the shaft.

10. A drilling instrument as in claim 9, wherein the shaft is a hollow tube and has a crimp along the longitudinal axis to create a solid portion of the body.

11. A drilling instrument as in claim 9, wherein the shaft body is solid from 3–15 mm from the point to the proximal end.

* * * * *